(12) United States Patent
Dickens et al.

(10) Patent No.: US 7,619,016 B2
(45) Date of Patent: Nov. 17, 2009

(54) REMINERALIZING DENTAL CEMENTS

(75) Inventors: Sabine H. Dickens, Montgomery Village, MD (US); Frederick C. Eichmiller, Ijamsville, MD (US)

(73) Assignee: ADA Foundation, Chicago, IL (US)

( * ) Notice: Subject to any disclaimer, the term of this patent is extended or adjusted under 35 U.S.C. 154(b) by 516 days.

(21) Appl. No.: 10/883,011

(22) Filed: Jul. 2, 2004

(65) Prior Publication Data

US 2005/0020720 A1   Jan. 27, 2005

Related U.S. Application Data

(60) Provisional application No. 60/484,404, filed on Jul. 2, 2003.

(51) Int. Cl.
*A61K 6/083*   (2006.01)
*A61C 5/00*    (2006.01)

(52) U.S. Cl. .................. 523/117; 523/118; 433/2; 433/228.1

(58) Field of Classification Search ................ 523/117, 523/118; 433/2, 228.1
See application file for complete search history.

(56) References Cited

U.S. PATENT DOCUMENTS

| | | | |
|---|---|---|---|
| 4,518,430 A | 5/1985 | Brown et al. | |
| 4,542,167 A | 9/1985 | Aoki | |
| 4,542,172 A | 9/1985 | Jochum et al. | |
| 4,612,053 A | 9/1986 | Brown et al. | |
| 4,668,295 A | 5/1987 | Bajpai | |
| 4,684,673 A | 8/1987 | Adachi | |
| 4,705,476 A * | 11/1987 | Blair | 433/171 |
| 4,746,686 A | 5/1988 | Waller | |
| 4,813,876 A | 3/1989 | Wang | |
| 4,832,745 A | 5/1989 | Antonucci | |
| 4,886,843 A | 12/1989 | Walton | |
| 5,129,905 A | 7/1992 | Constantz | |
| 5,218,035 A | 6/1993 | Liu | |
| 5,444,104 A * | 8/1995 | Waknine | 522/24 |
| 5,496,399 A | 3/1996 | Ison et al. | |
| 5,569,490 A | 10/1996 | Imura et al. | |
| 5,603,922 A | 2/1997 | Winston et al. | |
| 5,614,175 A | 3/1997 | Winston et al. | |
| 5,652,016 A | 7/1997 | Imura et al. | |
| 5,695,729 A | 12/1997 | Chow et al. | |
| 5,782,971 A | 7/1998 | Constantz et al. | |
| 5,814,681 A | 9/1998 | Hino et al. | |
| 5,817,296 A | 10/1998 | Winston et al. | |
| 5,833,957 A | 11/1998 | Winston et al. | |
| 5,846,312 A | 12/1998 | Ison et al. | |
| 6,309,221 B1 | 10/2001 | Jensen | |
| 6,353,039 B1 * | 3/2002 | Rheinberger et al. | 523/109 |
| 6,375,935 B1 * | 4/2002 | Constantz | 424/57 |
| 6,398,859 B1 | 6/2002 | Dickens et al. | |
| 6,413,498 B1 | 7/2002 | Malmagro | |
| 6,500,004 B2 * | 12/2002 | Jensen et al. | 433/228.1 |
| 6,605,651 B1 * | 8/2003 | Stangel et al. | 523/116 |
| 6,649,669 B2 * | 11/2003 | Dickens | 522/76 |
| 6,787,584 B2 * | 9/2004 | Jia et al. | 523/115 |
| 7,166,652 B2 * | 1/2007 | Pearson et al. | 523/116 |
| 7,226,960 B2 * | 6/2007 | Jia | 523/115 |
| 2002/0045678 A1 * | 4/2002 | Lopez et al. | 523/116 |
| 2003/0149129 A1 | 8/2003 | Dickens | |
| 2005/0196726 A1 * | 9/2005 | Fischer | 433/224 |

FOREIGN PATENT DOCUMENTS

| | | |
|---|---|---|
| JP | 2-250809 | 10/2000 |
| WO | WO 02/15848 | 2/2002 |

OTHER PUBLICATIONS

Brown & Chow, "A New Calcium Phosphate, Water-Setting Cement," *Cements Res. Progr.* 1986, pp. 351-379.

Dickens-Venz et al., "Physical and chemical properties of resin-reinforced calcium phosphate cements," *Dent. Mater.* 10, 100-06, Mar. 1994.

Dickens et al., "Mechanical properties and biochemical activity of remineralizing resin-based Ca-$PO_4$ cements," *Dental Materials* 29, 558-66, 2003.

* cited by examiner

*Primary Examiner*—Tae H Yoon
(74) *Attorney, Agent, or Firm*—Banner & Witcoff, Ltd.

(57) ABSTRACT

Remineralizing dental cements contain source(s) of calcium and phosphate ions, adhesive resin monomers, reinforcing base resin monomers, and catalysts able to initiate the polymerization of the adhesive and reinforcing base resin monomers. Such dental cements can be used as orthodontic cements, crown and bridge cements, adhesives, sealants, cavity liners, and protective coatings. The release of calcium and phosphate ions and, optionally, fluoride ions, protects tooth structure from demineralization, a precursor of tooth decay.

4 Claims, 4 Drawing Sheets

FIG. 1

FIG. 2A (left), 2B (right)

REMINERALIZING DENTAL CEMENTS

This application claims the benefit of and incorporates by reference co-pending provisional application Ser. No. 60/484,404 filed Jul. 2, 2003.

FIELD OF THE INVENTION

The invention relates to remineralizing dental cements, which can be used as orthodontic cements, crown and bridge cements, adhesives, sealants, cavity liners, and protective coatings.

BACKGROUND OF THE INVENTION

It is well known that during and after orthodontic treatment a great number of the teeth bonded with composite cement show signs of demineralization of various degrees all the way to the presence of cavitated lesions. See, e.g., Mitchell et al., *Dent. Mater.* 11, 317-22, 1995. The greatest problems arise from plaque accumulating around the edges of the brackets, which are difficult to clean. Demineralization also occurs, for example, around bridges, crowns, and other restorative devices and at the site of caries lesions.

There is a need in the art for a strongly adhering material which would protect tooth structure adjacent to brackets or restorative devices and which would counteract the deleterious effects of bacterial acids by actively promoting remineralization.

BRIEF SUMMARY OF THE INVENTION

One embodiment of the invention is a remineralizing dental cement comprising a resin monomer component, at least one polymerization initiator, a source of calcium ions, and a source of phosphate ions. The resin monomer component comprises a polymerizable reinforcing base resin monomer, a polymerizable adhesive resin monomer, and, optionally, a polymerizable diluent monomer. The content of the polymerizable adhesive resin monomer is between about 5% and about 65% by weight of the resin monomer component. The content of the source of calcium ions and the source of phosphate ions is at least about 5% but less than 75% by weight of the cement.

Another embodiment of the invention is a method of making a remineralizing dental cement. The method comprises mixing a paste A with a paste B. Paste A comprises a polymerizable reinforcing base resin monomer, a first polymerization initiator, and, optionally, a first polymerizable diluent monomer. Paste B comprises a polymerizable adhesive resin monomer, a second polymerization initiator, and, optionally, a second polymerizable diluent monomer. At least one of paste A and paste B comprises a source of calcium ions and a source of phosphate ions in an amount to provide at least about 5% but less than 75% by weight of the calcium ions and the phosphate ions in the remineralizing dental cement. The content of the polymerizable adhesive resin monomer is between about 5% and about 65% by weight of the resin monomer component of the remineralizing dental cement.

Still another embodiment of the invention is a method of making a remineralizing dental cement. The method comprises mixing a paste and at least one polymerization initiator. The paste comprises: a polymerizable reinforcing base resin monomer; a polymerizable adhesive resin monomer; at least about 5% but less than 75% by weight of a source of calcium ions and a source of phosphate ions; and, optionally a polymerizable diluent monomer. The content of the polymerizable adhesive resin monomer is between about 5% and about 65% by weight of the resin monomer component of the remineralizing dental cement.

Even another embodiment of the invention is a hardened remineralizing dental cement comprising a source of calcium ions; a source of phosphate ions; and a polymerized resin component. The polymerized resin component comprises a polymerized reinforcing base resin; and a polymerized adhesive resin. The content of the polymerized adhesive resin is between about 5% and about 65% by weight of the resin component and wherein the content of the source of calcium ions and the source of phosphate ions is at least about 5% but less than 75% by weight of the hardened cement.

Still another embodiment of the invention is a method of preparing a hardened mineralizing dental cement. The method comprises mixing a paste A with a paste B; paste A comprises a polymerizable reinforcing base resin monomer, a first polymerization initiator, and, optionally, a first polymerizable diluent monomer. Paste B comprises a polymerizable adhesive resin monomer, a second polymerization initiator, and, optionally, a second polymerizable diluent monomer. At least one of paste A and paste B comprises a source of calcium ions and a source of phosphate ions in an amount to provide at least about 5% but less than 75% by weight of the calcium ions and the phosphate ions in the remineralizing dental cement. The content of the polymerizable adhesive resin monomer is between about 5% and about 65% by weight of the resin monomer component of the remineralizing dental cement. The method further comprises initiating polymerization of the polymerizable reinforcing base resin monomers the polymerizable adhesive resin monomers, and, if present, copolymerization of the polymerizable diluent monomers with the polymerizable reinforcing base resin monomers and with the polymerizable adhesive resin monomers.

A further embodiment of the invention is a method of preparing a hardened mineralizing dental cement. The method comprises mixing a paste and at least one polymerization initiator; the paste comprises (a) a polymerizable reinforcing base resin monomer, (b) a polymerizable adhesive resin monomer, (c) at least about 5% but less than 75% by weight of a source of calcium ions and a source of phosphate ions, and, optionally (d) a polymerizable diluent monomer. The content of the polymerizable adhesive resin monomer is between about 5% and about 65% by weight of the resin monomer component of the remineralizing dental cement. The method further comprises initiating polymerization of the polymerizable reinforcing base resin monomers; the polymerizable adhesive resin monomers; and, if present, copolymerization of the polymerizable diluent monomers with the polymerizable reinforcing base resin monomers and with the polymerizable adhesive resin monomers.

Another embodiment of the invention is a method of preparing a hardened mineralizing dental cement. The method comprises contacting a paste with a source of radiation. The paste comprises (a) a polymerizable reinforcing base resin monomer; (b) a polymerizable adhesive resin monomer; (c) a photoinitiator; (d) at least about 5% but less than 75% by weight of a source of calcium ions and a source of phosphate ions; and, optionally (e) a polymerizable diluent monomer. The content of the polymerizable adhesive resin monomer is between about 5% and about 65% by weight of the resin monomer component of the remineralizing dental cement.

Even another embodiment of the invention is a kit for preparing a remineralizing dental cement. The kit comprises (a) components of a paste A, (b) components of paste B; and, optionally, (c) instructions for mixing paste A with paste B to form the remineralizing dental cement. The components of paste A are (1) a polymerizable reinforcing base resin monomer; (2) a first polymerization initiator; and, optionally, (3) a first polymerizable diluent monomer. The components of a paste B are (1) a polymerizable adhesive resin monomer; (2) a second polymerization initiator; and, optionally, (3) a second polymerizable diluent monomer. The components of at least one of paste A and paste B comprise a source of calcium ions and a source of phosphate ions in an amount to provide at least about 5% but less than 75% by weight of the calcium ions and the phosphate ions in the remineralizing dental cement. The content of the polymerizable adhesive resin monomer is between about 5% and about 65% by weight of the resin monomer component of the remineralizing dental cement.

Yet another embodiment of the invention is a kit for preparing a remineralizing dental cement. The kit comprises a paste comprising a polymerizable reinforcing base resin monomer; a polymerizable adhesive resin monomer, wherein the content of the polymerizable adhesive resin monomer is between about 5% and about 65% by weight of the resin monomer component of the remineralizing dental cement; at least about 5% but less than 75% by weight of a source of calcium ions and a source of phosphate ions; at least one photoinitiator; and, optionally a polymerizable diluent monomer.

A kit for preparing a remineralizing dental cement. The kit comprises a paste comprising (a) a polymerizable reinforcing base resin monomer; (b) a polymerizable adhesive resin monomer, wherein the content of the polymerizable adhesive resin monomer is between about 5% and about 65% by weight of the resin monomer component of the remineralizing dental cement; (c) at least about 5% but less than 75% by weight of a source of calcium ions and a source of phosphate ions; and, optionally (d) a polymerizable diluent monomer. The kit optionally comprises at least one polymerization initiator.

Even another embodiment of the invention is a method of promoting remineralization of at least one portion of a tooth comprising contacting the at least one portion of the tooth with a remineralizing dental cement. The remineralizing dental cement comprises a resin monomer component, at least one polymerization initiator, a source of calcium ions, and a source of phosphate ions. The resin monomer component comprises a polymerizable reinforcing base resin monomer, a polymerizable adhesive resin monomer, and, optionally, a polymerizable diluent monomer. The content of the polymerizable adhesive resin monomer is between about 5% and about 65% by weight of the resin monomer component. The content of the source of calcium ions and the source of phosphate ions is at least about 5% but less than 75% by weight of the cement. The at least one portion is thereby remineralized.

A further embodiment of the invention is a method of adhering an orthodontic bracket to a tooth comprising contacting at least one of the tooth or the orthodontic bracket with a remineralizing dental cement. The remineralizing dental cement comprises a resin monomer component, at least one polymerization initiator, a source of calcium ions, and a source of phosphate ions. The resin monomer component comprises a polymerizable reinforcing base resin monomer, a polymerizable adhesive resin monomer, and, optionally, a polymerizable diluent monomer. The content of the polymerizable adhesive resin monomer is between about 5% and about 65% by weight of the resin monomer component. The content of the source of calcium ions and the source of phosphate ions is at least about 5% but less than 75% by weight of the cement. The orthodontic bracket thereby adheres to the tooth.

Still another embodiment of the invention is a method of adhering a crown to a tooth comprising contacting at least one of the tooth or the crown with a remineralizing dental cement. The remineralizing dental cement comprises a resin monomer component, at least one polymerization initiator, a source of calcium ions, and a source of phosphate ions. The resin monomer component comprises a polymerizable reinforcing base resin monomer, a polymerizable adhesive resin monomer, and, optionally, a polymerizable diluent monomer. The content of the polymerizable adhesive resin monomer is between about 5% and about 65% by weight of the resin monomer component. The content of the source of calcium ions and the source of phosphate ions is at least about 5% but less than 75% by weight of the cement. The crown thereby adheres to the tooth.

Even another embodiment of the invention is a method of adhering a bridge to at least one tooth comprising contacting at least one of the bridge or the at least one tooth with a remineralizing dental cement. The remineralizing dental cement comprises a resin monomer component, at least one polymerization initiator, a source of calcium ions, and a source of phosphate ions. The resin monomer component comprises a polymerizable reinforcing base resin monomer, a polymerizable adhesive resin monomer, and, optionally, a polymerizable diluent monomer. The content of the polymerizable adhesive resin monomer is between about 5% and about 65% by weight of the resin monomer component. The content of the source of calcium ions and the source of phosphate ions is at least about 5% but less than 75% by weight of the cement. The bridge thereby adheres to the at least one tooth.

The invention thus provides strongly adhering materials that protect tooth structure and that counteract the deleterious effects of bacterial acids by actively promoting remineralization.

BRIEF DESCRIPTION OF THE FIGURES

FIG. 2. Graph showing lesion mineral content as a function of distance from the bracket edge.

FIG. 4A, fluoride release from the fluoride-containing orthodontic Ca—$PO_4$ cement and from a commercial orthodontic bonding material (PD; Pulpdent Ortho-Choice OBA; Pulpdent Corp., Watertown, Mass.). FIG. 4B, calcium ion release from fluoride free (NF) and fluoride-containing (F) orthodontic Ca—$PO_4$ cement. FIG. 4C, phosphate ion release from fluoride free (NF) and fluoride-containing (F) orthodontic Ca—$PO_4$ cement.

DETAILED DESCRIPTION OF THE INVENTION

The present invention provides remineralizing dental cement formulations which act as strong dental adhesives and which prevent or reduce demineralization by actively releasing calcium and phosphate ions. Such cements can be used, inter alia, to adhere orthodontic brackets to tooth structure, to cement fixed dental prostheses, as a protective tooth coating (including on a smooth surface of a tooth), as a pit and/or fissure sealant, as a dental filling material, and as a protective cavity base or liner.

Because they release calcium and phosphate ions and, optionally, fluoride ions, remineralizing cements of the invention have several advantages over existing adhesives, cements, liners, or coatings. The release of calcium and phosphate ions, and also the release of fluoride ions, protects tooth structure from demineralization, a precursor of tooth decay, which is a particular threat to tooth structure surrounding brackets attached to tooth surfaces for orthodontic procedures. Orthodontic demineralization is a major adverse consequence of orthodontic treatment. The present invention provides a bonding material with the inherent ability to inhibit or repair this damage, thereby providing a major health benefit.

Remineralizing cements of the invention also stimulate repair of early lesions by remineralizing mineral deficient enamel or dentin. The cements protect the enamel surrounding brackets, the enamel around the margins of cemented dental prostheses to which caries-stimulating plaque easily adheres, the enamel near or under dental fillings, the enamel under and surrounding protective coatings, as well as protecting adjacent tooth structures. Remineralizing cements can also be used as a temporary filling material to control dental decay until more permanent restorations can be placed.

Crown and bridge cements have little or no inherent caries preventing features; when used as a crown or bridge cement, cements of the invention provide a caries preventing benefit. Cements of the invention also provide caries inhibiting and/or repair benefits when used as pit and fissure sealants, protective tooth coatings, cavity bases and liners, temporary filling materials, and dentin and enamel adhesives. Remineralizing adherent slow release devices made from these materials can be bonded directly to teeth for therapeutic effect.

Dental fillings provided in settings where traditional dental equipment and facilities are not available often require manual removal of decay using hand instruments and the placement of self-setting materials, such as glass ionomers to replace the missing tooth structure caused by the decay. The non-mechanical removal of decay often leaves a substantial amount of demineralized tooth structure due to the inefficiency of the manual instrumentation. Typical glass ionomer fillings lack the ability to remineralize this tissue. A remineralizing cement of the invention used as a filling material has the advantage of being able to remineralize this remaining demineralized tissue and prevent subsequent decay. Optionally, remineralizing cements of the invention can be reinforced to provide strength to adequate withstand chewing forces.

Remineralizing cements of the invention can be used as temporary filling materials with the advantage of being capable of remineralizing demineralized tooth structure left behind in deep cavity preparations. In very deep cavity preparations, demineralized dentin is often left at the base of the cavity to prevent exposing the pulp during the decay removal process. A temporary restoration is then placed until it is determined that no permanent damage has occurred to the pulp of the tooth. The temporary restoration is then removed and replaced by a more permanent restoration. The cements disclosed herein have the advantage of providing a strong base material that repairs the demineralized dentin left behind in the preparation process. The cement can then be partially removed, leaving the deepest material intact and covered with the more permanent restoration. This procedure eliminates the risk of pulp damage associated with removal of the entire temporary restoration and provides a method of repairing damaged tooth tissue.

Composition of Remineralizing Cements

Before setting, remineralizing cement formulations of the invention comprise a source of calcium ions and a source of phosphate ions; a resin monomer component that comprises a polymerizable adhesive resin monomer, a polymerizable reinforcing base resin monomer, and, optionally, a polymerizable diluent monomer; and at least one polymerization initiator. The content of the polymerizable adhesive resin monomer is at least about 5%, preferably between about 5% and about 65%, by weight of the resin monomer component. The content of the source of calcium ions and the source of phosphate ions is at least about 5% but less than 75% by weight of the cement. Optionally, as described below, cement formulations of the invention can contain other additives. The percent by weight of all components of the cement formulations add up to 100% (i.e., no solvent is added).

When used as crown or bridge luting cements, cement formulations of the invention preferably have a film thickness of less than about 100 μm, preferably less than about 90 μm, less than about 80 μm, less than about 70 μm, less than about 60 mm, less than about 50 μm, less than about 40 μm, less than about 30 μm, or less than about 20 μm, typically about 20 to about 40 μm. When used as an orthodontic cement, film thickness can be greater than about 100 μm.

During and after setting, cement formulations of the invention provide a neutral to slightly basic pH, freely available calcium and phosphate ions, and, depending on the additives, slow and continuous release of fluoride. The calcium and phosphate ions are taken up by tooth dentin and enamel to form hydroxyapatite when exposed to moisture. The monomers harden on command into a polymer network. Hardened remineralizing cements primarily contain calcium phosphates and a cross-linked polymer matrix.

When hardened, cements of the invention preferably have a flexural strength of at least 40 Newton/mm$^2$, even more preferably at least 50 Newton/mm$^2$. Hardened cements, whether made using two pastes or one paste, contain a source of calcium ions, a source of phosphate ions, and a polymerized resin. The content of the source of calcium ions and the source of phosphate ions is at least about 5% but less than 75% by weight of the hardened cement. The content of the adhesive component of the polymerized resin is at least about 5% and up to about 65% by weight of the total polymerized resin.

Sources of Calcium and Phosphate Ions

If two pastes are used to mix a remineralizing cement, the sources of the calcium and phosphate ions in the two pastes can be the same or different. In either case, the total content of the source of calcium ions and the source of phosphate ions in the mixed cement and in the hardened cement is at least about 5%, about 10%, about 15%, about 20%, about 25%, about 30%, about 35%, about 40%, about 45%, about 50%, about 55%, about 60%, about 65%, or about 70% by weight but is less than 75% by weight. In some embodiments, the content of the source of calcium and phosphate ions in the cement is less than about 73%, 70%, 60%, 50%, or 40% by weight.

The source of the calcium ions and the source of the phosphate ions can be a single compound or can be a mixture of single compounds. In fact, an advantage of the cements disclosed herein is that, if desired, they can be formulated using a single compound as the source of both the calcium ions and the phosphate ions; the single compound is not required to react with any other calcium phosphate compound within the cement. Suitable single sources of calcium and phosphate ions include, but are not limited to, dicalcium phosphate anhydrous, tetracalcium phosphate, dicalcium phosphate dihydrate, tricalcium phosphate, and mixtures thereof. In one embodiment (shown in Table 1), a single compound (dicalcium phosphate anhydrous; DCPA) is the source of the calcium ions and the phosphate ions in both paste A and paste B. The sources of ions in the two pastes, however, need not be the same.

Suitable separate sources of the calcium ions and phosphate ions are, for example, calcium chloride, calcium sulfate, calcium aluminosilicate, calcium carbonate, calcium chloride, calcium ascorbate, calcium oxide and either sodium phosphate, di-potassium phosphate, and tri-potassium phosphate. When supplying the calcium and phosphate ions from separate sources, care should be exercised to supply the sources in a non-hydroxyapatite-producing ratio, so that the calcium and phosphate ions are freely available for release.

The particle size of the sources of calcium and phosphate ions depends on the use to which the dental cement will be put. For example, particles for crown and bridge cements typically are under 20 μm to achieve the proper film thickness for the final cement layer. Particle sizes for orthodontic cements have a wider range, as is known in the art. The choice of particle size for a particular application is within the ability of the skilled practitioner.

Resin Monomer Component

The resin monomer component contains polymerizable reinforcing base resin monomers, at least 5% and, preferably, between about 5% and about 65% (e.g., about 5, 10, 15, 20, 25, 30, 35, 40, 45, 50, 55, 60, 62, or 65%), by weight polymerizable adhesive resin monomers and, optionally, one or more polymerizable diluent monomers. The ratio of polymerizable adhesive resin monomers to reinforcing base resin monomers is not critical; however, composition of the resin monomer component preferably is adjusted for maximum calcium and phosphate ion release from the source(s) of these ions.

Polymerizable Reinforcing Base Resin Monomers

Suitable polymerizable reinforcing base resin monomers include but are not limited to, 1,6-bis(methacryloxy-2-ethoxycarbonylamino)-2,4,4-trimethylhexane (urethane dimethacrylate, UDMA), 2,2-bis[p-(2'-hydroxy-3'-methacryloxypropoxy)phenylene]-propane (bis-GMA), ethoxylated bisphenol A dimethacrylate (EBPADMA), and mixtures thereof.

Polymerizable Adhesive Resin Monomers

Typically, a polymerizable adhesive resin monomer is an addition reaction product formed by the reaction between an anhydride and a hydroxyl-containing polymerizable monomer. Suitable polymerizable adhesive resin monomers include, but are not limited to, pyromellitic dianhydride GDM (glycerol dimethacrylate) adduct (PMGDM), pyromellitic dianhydride HEMA (HEMA=2-hydroxyethyl methacrylate) adduct (PMDM), biphenyl dianhydride GDM adduct (BP-GDM), biphenyl dianhydride HEMA adduct (BP-HEMA), benzophenone-3,3',4,4'-tetracarboxylic dianhydride GDM adduct (BPh-GDM), benzophenone-3,3',4,4'-tetracarboxylic dianhydride HEMA adduct (BPh-HEMA), bicyclo[2.2.2]oct-7-ene-2,3,5,6-tetracarboxylic dianhydride GDM adduct (BCOE-GDM), bicyclo[2.2.2]oct-7-ene-2,3,5,6-tetracarboxylic dianhydride HEMA adduct (BCOE-HEMA), 4,4'-oxydibenzoic dianhydride GDM adduct (ODB-GDM), 4,4'-oxydibenzoic dianhydride HEMA adduct (ODB-HEMA); 5-(2,5dioxotetrahydro-3-furanyl)-3-cyclohexene-1,2-dicarboxylic anhydride GDM adduct (B4400-GDM), 5-(2,5dioxotetrahydro-3-furanyl)-3-cyclohexene-1,2-dicarboxylic anhydride HEMA adduct (B4400-HEMA), 4,4'-(4,4'-Isopropylidenediphenoxy)bis(phthalic anhydride)-GDM adduct (IPA-GDM), 4,4'-(4,4'-Isopropylidenediphenoxy)bis(phthalic anhydride)-HEMA adduct (IPA-HEMA), phthalic anhydride GDM adduct (PhTh-GDM), Phthalic anhydride HEMA adduct (PhTh-HEMA), pyromellitic dianhydride GDA (glycerol diacrylate) adduct (PMGDA), pyromellitic dianhydride-HEA (hydroxyethyl acrylate) adduct (PMDAc), biphenyl dianhydride GDA adduct (BP-GDA), biphenyl dianhydride HEA adduct (BP-HEA), benzophenone-3,3',4,4'-tetracarboxylic dianhydride GDA adduct (BPh-GDA), benzophenone-3,3',4,4'-tetracarboxylic dianhydride HEA adduct (BPh-HEA), bicyclo[2.2.2]oct-7-ene-2,3,5,6-tetracarboxylic dianhydride GDA adduct (BCOE-GDA), bicyclo[2.2.2]oct-7-ene-2,3,5,6-tetracarboxylic dianhydride HEA adduct (BCOE-HEA), 5-(2,5dioxotetrahydro-3-furanyl)-3-cyclohexene-1,2-dicarboxylic anhydride GDA adduct (B4400-GDA), 5-(2,5dioxotetrahydro-3-furanyl)-3-cyclohexene-1,2-dicarboxylic anhydride HEA adduct (B4400-HEA), 4,4'-(4,4'-Isopropylidenediphenoxy)bis(phthalic anhydride)-GDA adduct (IPA-GDA), 4,4'-(4,4'-Isopropylidenediphenoxy)bis(phthalic anhydride)-HEA adduct (IPA-HEA), phthalic anhydride GDA adduct (PhTh-GDA), phthalic anhydride HEA adduct (PhTh-HEA), and mixtures thereof.

PMGDM is a preferred adhesive resin monomer; a preferred concentration of PMGDM is 45% to 56% of the resin monomer component.

Polymerizable Diluent Monomers

If desired, a polymerizable diluent monomer can be included to provide adequate strength and to control viscosity. In a two-paste formulation, a polymerizable diluent monomer can be either in paste A, paste B, or both, in concentrations of 0 to about 50% by weight. Useful polymerizable diluent monomers include, but are not limited to, 2-hydroxyethylmethacrylate (HEMA), glycerol dimethacrylate (GDM), ethyl-α-hydroxymethyl acrylate (EHMA), tetrahydrofurfuryl methacrylate (THFM), hydroxypropyl methacrylate (HPMA), 2-hydroxyethylacrylate (HEA), glycerol diacrylate (GDA), tetrahydrofurfuryl acrylate (THFA), hydroxypropyl acrylate (HPMA), triethyleneglycol dimethacrylate (TEGDMA), tetraethyleneglycol dimethacrylate (TETDMA), benzyl methacrylate (BMA), 1,10,-decamethylene dimethacrylate (DMDMA), hexamethylene dimethacrylate (HMDMA), 1,10-decamethylene dimethacrylate (DMDMA), and mixtures thereof.

Polymerization Initiators

Polymerization initiators include three types, photoinitiators, catalysts, and co-initiators.

Photoinitiators are compounds that can initiate the polymerization of resin monomers after being irradiated by light of a certain wavelength or band of wavelengths. Some types of photo-initiators can initiate this polymerization when used alone and others require the use of a second co-initiator along with the photoinitiator. Photoinitiators can include camphorquinone, benzil, and mono- and bis(acylphosphine oxides), and derivatives thereof that will be excited by light of a wavelength in the range from 380 nm to 550 nm. UV photoinitiators include phosphineoxides and 2,2-dimethoxy-2-phenylacetophenone.

Catalysts are compounds that can chemically initiate the polymerization of resin monomers by reacting with second compound, commonly called a co-initiator or by the addition of heat. An example of a catalyst includes, but is not limited to, benzoyl peroxide (BP).

Co-initiators are compounds that react with a catalyst and/or a photoinitiator to accelerate polymerization of the resin monomers. Examples include (2-(4-dimethyl-aminophenyl) ethanol) (DMAPE), N,N—dimethylamino ethylmethacrylate, dimethylamino paratoluidine, and others known in the trade. Co-initiators can include tertiary amines of the general structure $R_1R_2$—N—$C_6H_4$—X, where the nitrogen substituents $R_1$ and $R_2$ may be the same or different, may be composed of an alkyl or an alkyl alcohol, and where X is an electron withdrawing group. Other amine accelerators, for example aliphatic tertiary amines, known in the art are also well suited for the purpose.

The polymerization initiators for the polymerization of resin monomers can be the same or different. In some two-paste embodiments (for example, the embodiment shown in Table 1) there is a photoinitiator (e.g., camphorquinone) and a co-initiator (e.g., DMAPE) in one paste (e.g., paste A). The co-initiator can also act as a polymerization accelerator for a catalyst (e.g., benzoyl peroxide=BPO) in the other paste (e.g., paste B). The other paste (e.g., paste B) also can contain a photoinitiator, such as camphorquinone.

Optional Additives

A source of fluoride ions can be included in remineralizing cements of the invention. The beneficial effect of fluoride on tooth hard tissues de- and remineralization has been well documented in in vivo and in vitro experiments (Ten Cate, 1984, 1990). In two-paste embodiments, the source of fluoride ions can be in paste A, in paste B, or can be added after mixing paste A and paste B together. Suitable sources of fluoride ions include, but are not limited to, $Na_2SiF_6$, $CaF_2$, $SrF_2$, NaF, $NaPO_3F$, $NaKF_6PO_3$, $K_2SiF_6$, $F_6NaP$, $NaSbF_6$, $KSbF_6$, $F_6KP$, and mixtures thereof The final concentration of a source of fluoride ions in a remineralizing cement preferably is about 2% by weight.

Other optional additives include inert fillers for controlling viscosity (e.g., titanium dioxide, tin dioxide, aluminum oxide, silica, zinc oxide, barium sulfate;) and pigments (e.g., metal oxides such as titanium dioxide). In a two-paste embodiment, any of these additives can be present in one or both pastes.

In addition to or in place of at least some of the source(s) of calcium and phosphate ions, pastes can be supplemented with a filler to increase strength and/or with an agent to increase radioopacity. Fillers include, but are not limited to, polymeric particles (e.g., commutated polymer powders or atomized polymer spheres, sol-gel processed polymer particles, any polymeric particulate), mineral particles, metal particles, and glass fillers. Suitable glass fillers include barium boroaluminosilicate glass, fluoroaluminosilicate glass, silica, silicate glass, quartz, barium silicate glass, strontium silicate glass, barium borosilicate glass, borosilicate glass, barium aluminofluorosilicate glass, lithium silicate, amorphous silica, barium magnesium aluminosilicate glass, barium aluminosilicate glass, strontium aluminum-borosilicate glass; strontium aluminofluorosilicate glass, amorphous silica, zirconium silicate glass, titanium silicate glass, and the like, as well as mixtures thereof. Glasses containing fluoride are useful because they also provide a source of fluoride ions. See U.S. Pat. Nos. 6,730,715 and 6,403,676. Fillers can have any morphology or shape, including spheres, regular or irregular shapes, fibers, filaments or whiskers, and the like.

Optionally, a reductive inhibitor or stabilizer, such as 2,6-di-t-butyl-4-methyl phenol (BHT), can be included to prevent premature polymerization and to extend shelf stability.

Methods of Making Remineralizing Cement Formulations

In some embodiments of the invention, remineralizing cements are made by mixing together two pastes (e.g., paste A and paste B) to form remineralizing cements. Paste A comprises a polymerizable reinforcing base resin monomer and a polymerization initiator, which can be a photoinitiator. Paste A optionally can contain a co-initiator. Paste B comprises a polymerizable adhesive resin monomer and a polymerization initiator, which can be a photoinitiator. Paste B optionally can contain a catalyst. At least one of paste A and paste B comprises a source of calcium ions and a source of phosphate ions in an amount to provide at least about 5% but less than 75% by weight of the calcium ions and the phosphate ions in the remineralizing dental cement. In these embodiments paste A, paste B, or both pastes A and B can contain a polymerizable diluent monomer.

In other embodiments, remineralizing cements are made by mixing together one paste and at least one polymerization initiator, which can be a photoinitiator. In these embodiments, the paste comprises a polymerizable reinforcing base resin monomer, a polymerizable adhesive resin monomer, a total of at least about 5% but less than 75% by weight of a source of calcium ions and a source of phosphate ions, and, optionally, a polymerizable diluent monomer. The paste also can contain a co-initiator or can contain a co-initiator and a catalyst.

In still other embodiments, remineralizing cements are made by initiating polymerization of the resin monomer components in a paste that comprises a photoinitiator. In these embodiments, the paste comprises a photoinitiator, a polymerizable reinforcing base resin monomer, a polymerizable adhesive resin monomer, a total of at least about 5% but less than 75% by weight of a source of calcium ions and a source of phosphate ions, and, optionally, a polymerizable diluent monomer. The paste also can contain a co-initiator.

If two pastes are used, the two pastes can be conveniently mixed together, for example, by hand spatulation on a glass slab or paper pad using a metal or plastic spatula.

Alternatively, mechanical mixing devices, such as syringe or plastic vortex mixing tips, can be used. Mixing time is not critical, as long as mixing is carried out for a period of time that is shorter than the working time. Mixing preferably does not heat the mixture and preferably blends the two pastes thoroughly. The preferred working time is application-dependent and can be varied by varying the concentration of initiators and inhibitors, as is known in the art. These principles apply also to mixing a one-paste formulation with one or more polymerization initiators and inhibitors or stabilizers.

In certain preferred two-paste embodiments, the mixture of paste A and paste B is in a ratio of about 1:1.5 by weight. This ratio can be altered, however, as long as the ratio of initiators is also altered adjusted to achieve the desired working and setting times. Such alterations are well within the skill of the formulator. See Example 1 for an example of a two-paste embodiment that can be mixed in a ratio of about 1:1 by weight.

Kits

The invention also provides kits which contain components of cement formulations of the invention and can include instructions for making and using the cements. Components of each of paste A and paste B can be packaged, for example, in separate bulk containers or in syringes. Optionally, components of paste A and paste B can be provided in a two-barrel syringe.

Other kits comprise a paste comprising a polymerizable reinforcing base resin monomer, a polymerizable adhesive resin monomer, at least about 5% but less than 75% by weight of a source of calcium ions and a source of phosphate ions, at least one photoinitiator, and, optionally a polymerizable diluent monomer. The content of the polymerizable adhesive resin monomer is between about 5% and about 65% by weight of the resin monomer component of the remineralizing dental cement. The paste optionally can contain a co-initiator.

Other kits comprise a paste comprising a polymerizable reinforcing base resin monomer; a polymerizable adhesive resin monomer, at least about 5% but less than 75% by weight of a source of calcium ions and a source of phosphate ions; and, optionally a polymerizable diluent monomer. The content of the polymerizable adhesive resin monomer is between about 5% and about 65% by weight of the resin monomer component of the remineralizing dental cement. The kit optionally comprises (packaged separately) at least one polymerization initiator and, optionally, a co-initiator and a catalyst.

Other components of kits can include one or more of any of the following items: an etching gel for conditioning the tooth surface, a brush, an applicator for the cement, a syringe tip and/or mixing tip, a spatula for either mixing or dispensing the cement, a paper mixing pad, and a supplemental adhesive.

All patents, patent applications, and references cited in this disclosure are expressly incorporated herein by reference.

The above disclosure generally describes the present invention. A more complete understanding can be obtained by reference to the following specific examples, which are provided for purposes of illustration only and are not intended to limit the scope of the invention.

EXAMPLE 1

Preparation of a Two-paste Adhesive Composition for Orthodontic Brackets

Two pastes as shown in Table 1 were mixed with an A:B ratio of 1:1.5 by weight. Chemically induced working time and setting time were measured with a computer-controlled thermocouple. The working time at room temperature was greater than 10 minutes. The setting time at 37° C. was 4 minutes.

TABLE 1

Two-paste adhesive composition to be mixed in a 1:1.5 weight ratio

| Paste A, wt % | | Paste B, wt % | |
|---|---|---|---|
| TEGDMA | 9.55 | PMGDM | 30.93 |
| UDMA | 28.64 | TEGDMA | 6.19 |
| DCPA | 61.11 | DCPA | 59.39 |
| DMAPE | 0.46 | CQ | 0.24 |
| CQ | 0.24 | BPO | 3.33 |
| | | BHT | 0.03 |

Table 2 shows a two-paste adhesive composition that can be mixed in a 1:1 weight ratio.

TABLE 2

Two-paste adhesive composition to be mixed in a 1:1 weight ratio

| Paste A, wt % | | Paste B, wt % | |
|---|---|---|---|
| TEGDMA | 9 | PMGDM | 35 |
| UDMA | 30 | TEGDMA | 11 |
| DCPA | 60 | UDMA | 25.5 |
| DMAPE | 0.6 | DCPA | 27.2 |
| CQ | 0.4 | BPO | 1 |
| | | BHT | 0.3 |

EXAMPLE 2

Measurement of Flexural Strength

Flexural strength of material prepared as described in the example above was measured at 24 hours on 2×2×25 mm bars in three-point bending. The flexural strength specimens were made by mixing paste A and paste B and light curing the molds for 20 seconds (s) on each side. They were stored in water at 37° C. Fluoride-containing pastes were also mixed for flexural strength specimens. Sodium hexafluorosilicate, $Na_2SiF_6$, was added to paste A to be 2.0% by weight of the entire A+B mixture. The bars were broken in a universal testing machine with a crosshead speed of 0.5 mm/min with a 100 N load cell.

The flexural strength of these specimens is shown in Table 3.

TABLE 3

| | Flexural strength | |
|---|---|---|
| | mean +/− s.d., MPa (Newton/mm$^2$) | n |
| with fluoride | 53.8 +/− 8.8 | 3 |
| without fluoride | 51.0 +/− 3.8 | 3 |

EXAMPLE 3

Shear Testing of Orthodontic Brackets Bound to Enamel with a Remineralizing Cement For bonding orthodontic brackets to enamel, extracted human incisors, canines, and third molars stored in chloramine T solution were used. The teeth were rinsed and lightly dried to remove most water. The buccal surface was etched with 10% $H_3PO_4$ gel for 20 seconds and rinsed for 10 seconds, followed by 5 seconds drying with an air stream.

Paste A (0.0178 g) was mixed with paste B (0.0267 g) for 30 seconds to form a remineralizing cement ("DCPA cement"). The compositions of pastes A and B are shown in Table 1. A small amount of the paste was pushed into the mesh on the back of orthodontic brackets (stainless steel, standard edgewise orthodontic bracket, 0° torque, 0° angulation; OSE Co., Inc., Gaithersburg, Md.), and then more paste was added to form a layer approximately 1 mm thick. The brackets were adapted to the tooth surfaces and firmly pushed so that excess adhesive was extruded from the sides. The excess was removed with an explorer. The adhesive was light cured for 20 seconds on each side of the bracket (80 seconds total). A pilot bracket drift experiment showed 2 of 5 brackets drifted over a 15 minute period.

Pulpdent Ortho-Choice OBA (Pulpdent Corp., Watertown, Mass.) was used as a control material. Brackets were mounted following manufacturers instructions. Each tooth was dried, and the surface etched with 35% $H_3PO_4$ Semi-Gel for 20 seconds, rinsed for 10 seconds, and dried with an air stream for 5 seconds. A very thin layer of bonding resin was applied to the tooth surface. A small amount of bracket adhesive was pressed in to the mesh on the back of the bracket and then more adhesive was added to make a thin layer. The bracket was pressed firmly on the tooth so that excess adhesive came out on the sides. The excess material was removed with an explorer, and each side was cured for 10 seconds (40 seconds total).

For long-term strength studies, the teeth were stored at 37° C. in saliva-like solution. Shear bond strength was tested at 20 minutes, 24 hours, and one week.

To mount the teeth for shear testing, an orthodontic wire bent at 90° was attached to the bracket on the tooth with an orthodontic rubber band. The wire was inserted into a surveyor in order to have the bracket aligned vertically. Acrylic tray material was placed in to a 2.5 cm tall tube. The tooth was lowered into the acrylic and remained there until the acrylic had set.

The embedded teeth and brackets were tested in a universal testing machine. The brackets were sheared off with a knife blade at a crosshead speed of 1 mm/min with a 5 kN load cell. The results are shown in Table 4. There was no statistical difference between the DCPA cement and the control material (2-way ANOVA, SNK p>0.05).

TABLE 4

Measured debonding force

| Adhesive, storage time | mean +/1 s.d., N | number of repetitions |
|---|---|---|
| DCPA cement, 20 minutes | 166.7 +/− 47.7 | 5 |
| DCPA cement, 24 hours | 176.3 +/− 29.0 | 5 |
| DCPA cement, 1 week | 128.2 +/− 19.3 | 5 |
| control, 20 minutes | 150.3 +/− 36.7 | 5 |
| control, 24 hours | 156.8 +/− 50.6 | 4 |
| control, 1 week | 186.1 +/− 34.4 | 5 |

EXAMPLE 4

Clinical Study

Eleven patients who consented to participate in this study had symmetric right and left premolars in the same arch scheduled for extraction as part of comprehensive orthodontic treatment. Thirty-eight teeth became available for the study. One tooth from each pair was randomly assigned to the control group (Transbond™ XT; 3M Unitek, Monrovia, Calif.) and the other to the experimental group (cement as shown in Table 1; "DCPA cement").

The facial surface of the teeth were cleaned with fluoride-free, oil-free pumice and rinsed with water. The teeth were isolated with cotton rolls and dried. The enamel was etched for 15 s with etching gel (3M Unitek, Monrovia, Calif.) and then rinsed for 15 s with water. A thin coating of Unitek™ Transbond XT primer (3M Unitek, Monrovia, Calif.) was placed on the etched surface with a disposable brush for the control cement only. The Ortho Organizers premolar bracket was cemented with either the control cement or the DCPA filled resin cement. The bracket was positioned on the facial surface of the crown and centered between the mesial and distal marginal ridges with the apical edge of the bracket approximately 1 mm from the gingiva. The cements were light cured for 60 seconds. The plaque-trapping annulus was a clear plastic ring with a diameter of 7 mm and a thickness of 0.75 mm. After the bonding procedure, the annulus was placed over the bracket to inhibit plaque removal from around the bracket. It was secured to the bracket with an elastic ligature.

Extractions occurred between 30 d and 180 d after placement. The extracted teeth were stored in a 2% sodium hypochlorite solution and analyzed by microradiography after assignment of random number codes. Sections of approximately 180 μm thickness were cut. Contact microradiographs were taken. Digital image analysis was conducted by the investigator at the Paffenbarger Research Center at the National Institute of Standards and Technology in Gaithersburg, Md.

Figure 1:
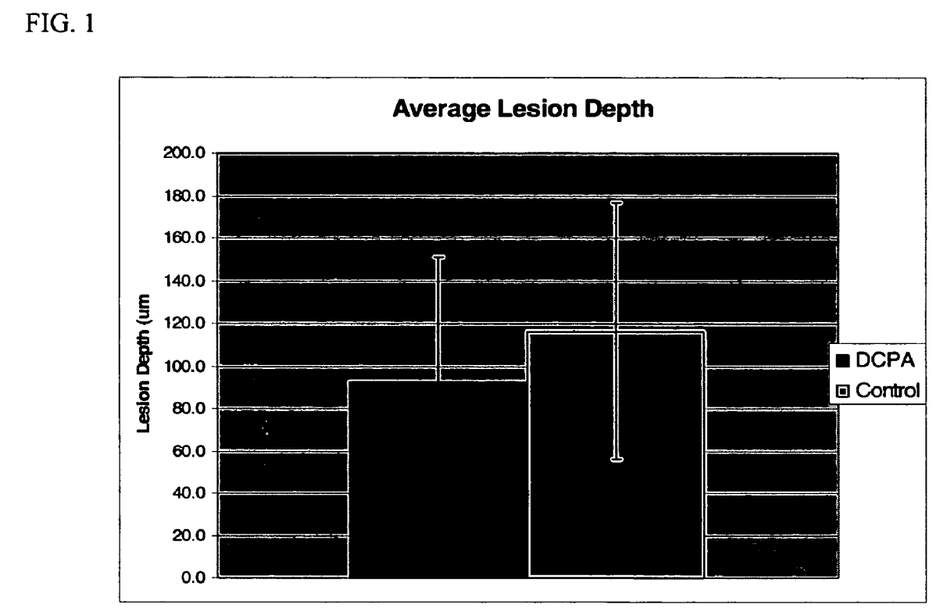
FIG. 1. Graph showing average cavitation over a range of distances from the bracket edge.

The lesions were evaluated for undermining cavitation and for lesion mineral content as a function of distance from the bracket edge. Negative numbers indicate a measurement underneath the bracket. The average depth on the control samples was 116.5±60.2 μm. The average depth on the DCPA samples was 92.5±58.5 μm. See FIG. 1. This outcome measure was associated with large variance values due to several factors. For example, the plastic sheet was frequently lost, and no control or record of these events was made. Second, the time of the bracket on each tooth varied from 30 d to about 180 d. After that time the plaque damage was so severe that any differences between experimental and control cement were lost. Despite these mishaps, a significant improvement due to using the experimental cement was shown when the mineral density was measured as a function of depth from the bracket edge or under the bracket. Of the 18 examined teeth with the experimental cement 7 teeth had undermining cavitation; under the control cement 11 teeth showed undermining cavitation.

Figure 2A:
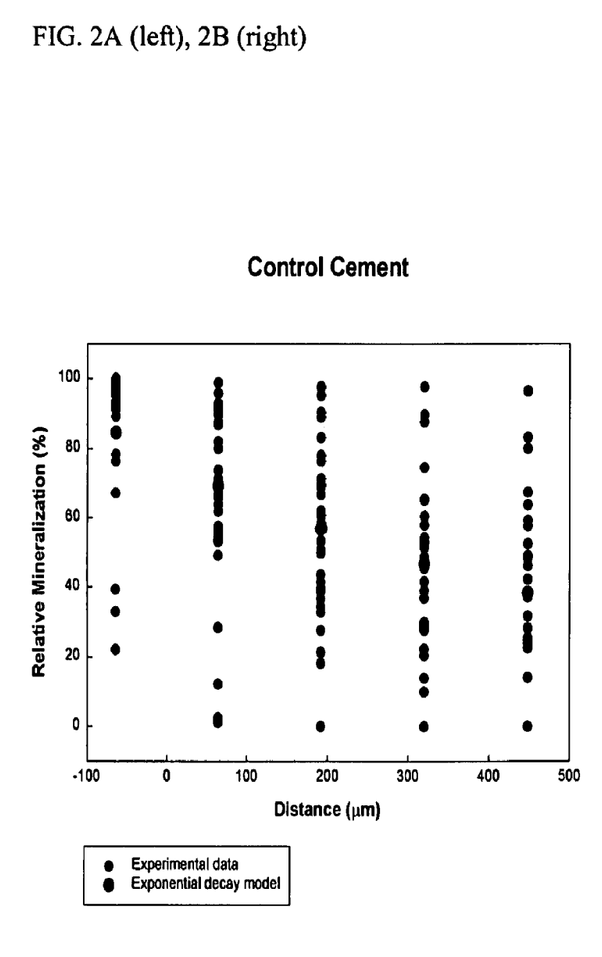
FIG. 2A, Graph showing lesion mineral content as a function of distance from the bracket edge for the control cement.
Figure 2B:
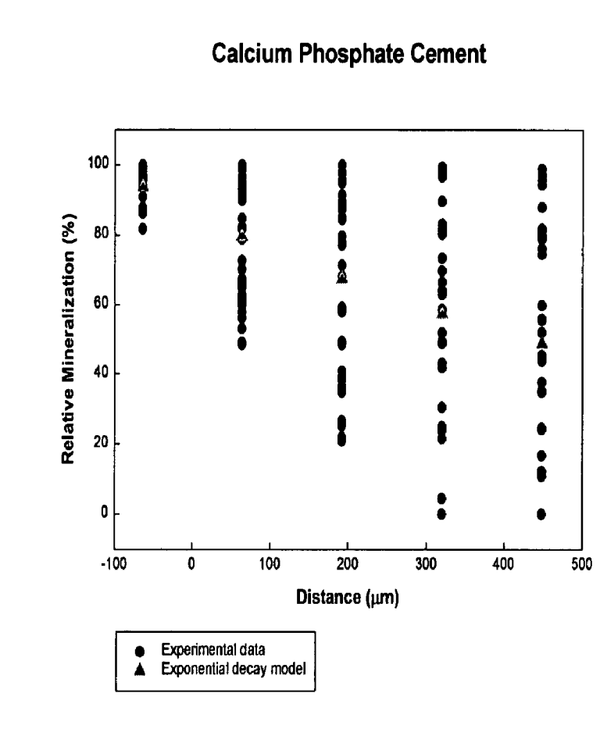
FIG. 2B, Graph showing lesion mineral content as a function of distance from the bracket edge for the experimental cement.
Figure 3:
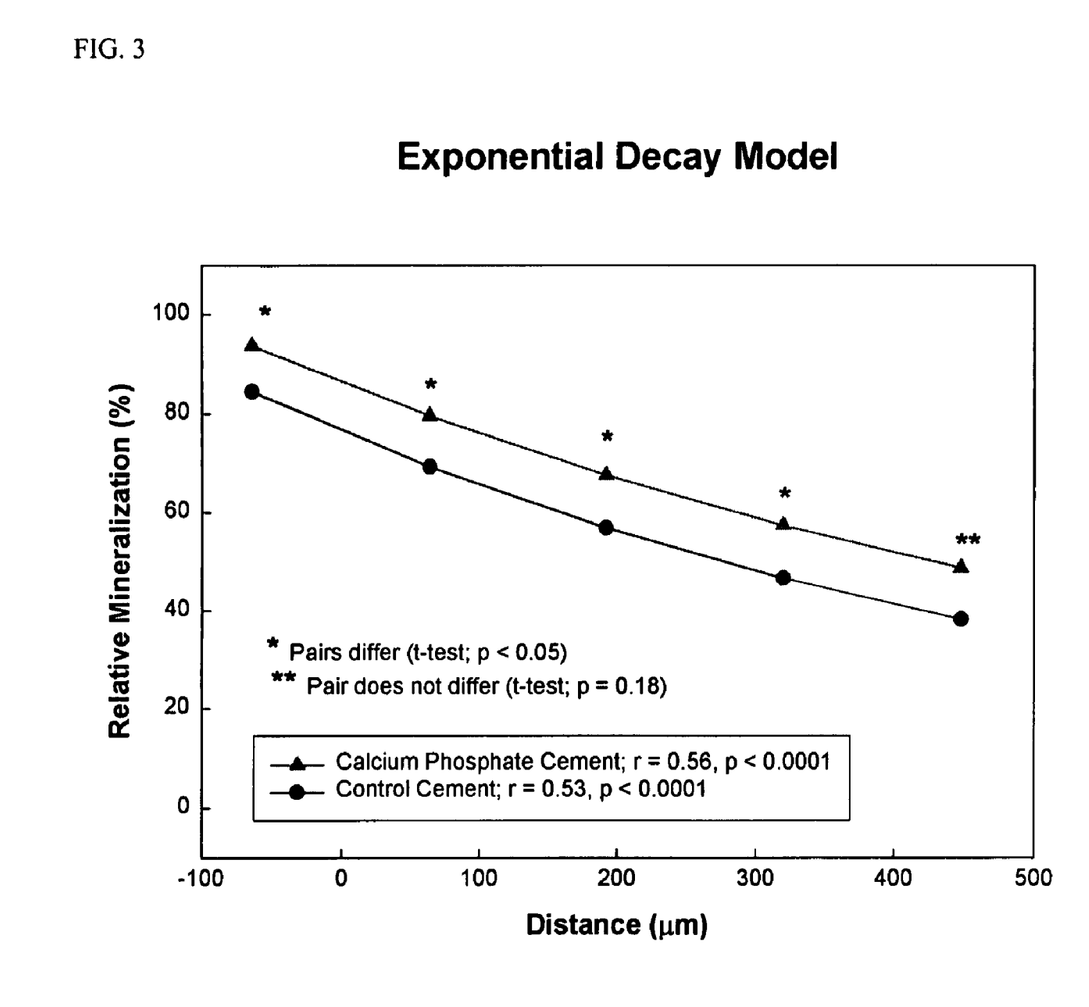
FIG. 3. Graph showing an exponential decay model of the lesion mineral content as a function of distance from the bracket edge. Data for the control cement (lower line) and for the experimental cement (upper line) are shown. The single asterisk indicates that up to a distance of 320 μm from the bracket edge the experimental cement affected significantly higher lesion mineral content than the control material.

FIGS. 2A and 2B show the relative mineral content (% of sound enamel). As can easily be seen, there is a lack of data points in the lower left corner of FIG. 2B (DCPA cement) to the graph on the left (FIG. 2A) showing the control data. Although purely descriptive, this visual interpretation of the data implies that there is a protective effect of DCPA very close to the bracket. Such an interpretation is consistent with the data in the exponential decay model, where differences exist until approximately 500 micrometers away from the cement. That is, in all but the last set of data (distance of 450 μm to the bracket edge), the DCPA cement led to higher enamel mineral content than the control cement. See FIG. 3.

The remineralization on extracted teeth was measured as described previously (Dickens et al., *Dental Materials* 29, 558-66, 2003). Briefly, extracted human molars were cut through the crowns parallel to the occlusal plane to expose a flat dentin surface. Four cavities extending partially into the surrounding enamel were drilled. The teeth were exposed to a demineralizing solution for 48 h prior to filling the cavities with either the orthodontic experimental cement or a calcium-phosphate free control material. After completion of the restorations, the teeth were immersed in saliva-like solution and incubated at 37° C. for 6 weeks.

Figure 4:
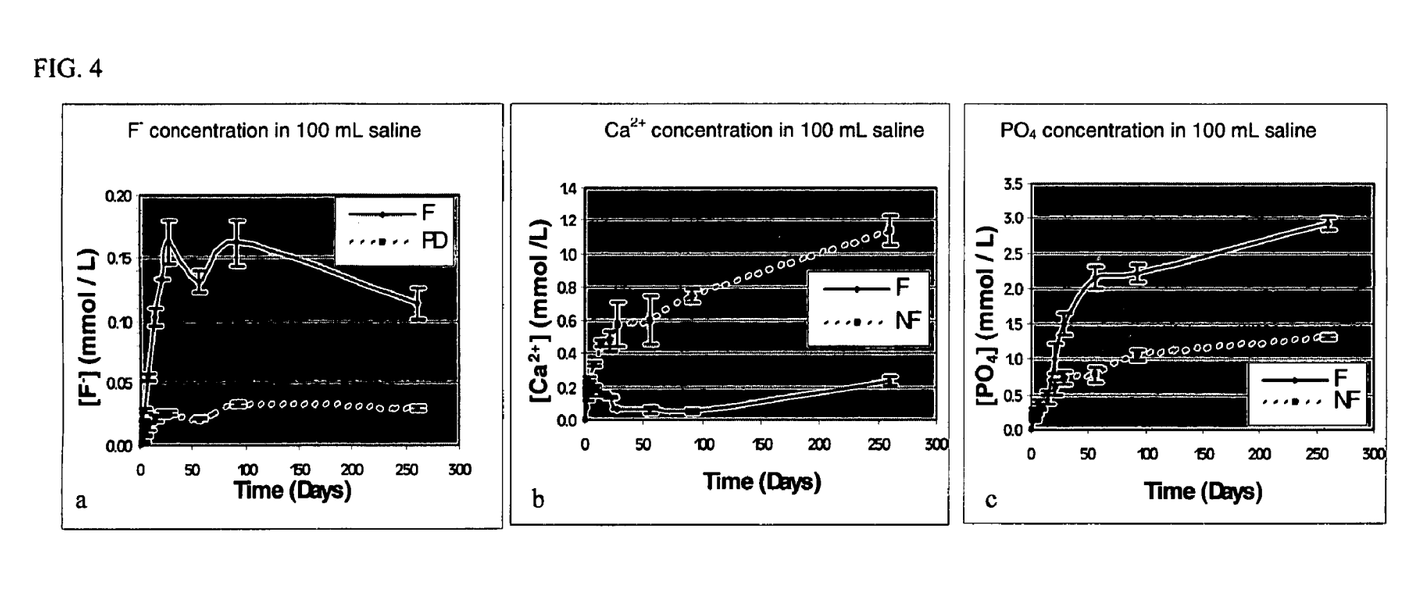
FIG. 4. Graph showing the fluoride, calcium and phosphate ion release in saline up to 270 days from the orthodontic cement.

Transverse sections 180 μm thick were cut, and microradiographs were taken. Imaging software was used to analyze the mineral content adjacent to the cement and compare it to the mineral content adjacent to the control material. The results showed that dentin walls had 33±18 (n=4) % remineralization. In enamel, only one tooth showed remineralization of 27%. The other teeth had either no enamel that could be measured or had further demineralization. FIG. 4 shows the fluoride, calcium and phosphate ion release into saline as a measure of the anticipated remineralization potential of the cement.

EXAMPLE 5

Effects of Varying Concentrations of PMGDM and DCPA on Film Thickness and Shear Bond Strength Measurement of bulk shear bond strength. Extracted human molars were mounted in plastic holders and sectioned through the upper third of the crown with a low-speed diamond saw to expose a flat dentin surface. The sectioned teeth were acid etched with 37% phosphoric acid for 15 seconds, rinsed, dried. The cements (Paste A and Paste B; see Example 1) were dispensed on to the mixing pad and mixed thoroughly.

A metal ring 2 mm high and 10 mm in diameter with a centric hole of 4 mm, which is covered on one side with Teflon tape was placed on the etched tooth surface. The metal disc was placed in a fitting device on the tooth surface and filled with the mixed cement. This was then placed under a load of around 150 N (Instron Corporation; Canton, Mass., USA) for 10 minutes to enhance the stabilization further. The samples were set-aside on the bench top for around 30 minutes before they were placed in a humidor at 37° C. for 24 hours.

The bonded metal rings were sheared off with a knife-edged blade at a crosshead speed of 0.5 mm/min using a universal testing machine (Instron Corporation; Canton, Mass., USA). The force needed to break the bond is divided by the bonded are. The shear bond strength is reported in Newton.mm².

Measurement of film bond strength. Extracted human molars were mounted in plastic holders and sectioned through the upper third of the crown with a low-speed diamond saw to expose a flat dentin surface. Metal discs measuring around 5 mm in diameter and 2 mm in length were sectioned from non-precious ceramic alloy cylinders, Rexillium® III (Pentron Inc, Wallingford, Conn.). The faces of the sectioned discs were polished on silicon carbide polishing paper with grit sizes 1000, 1200 and 2400 to obtain a smooth surface. The surfaces were then sand blasted using 50-micron aluminum oxide.

The sectioned teeth were acid etched with 37% phosphoric acid for 15 seconds, rinsed, dried. The cements (Paste A and Paste B; see Example 1) were dispensed on to the mixing pad and mixed thoroughly. A dab of the mixed cement was applied evenly to the prepared metal discs and placed on to the conditioned tooth surface. A metal cap (designed for the plastic holders with a smooth fit) was placed over the metal button to stablize and to distribute the cement under the buttons evenly. This was then placed under a load of around 20 N (Instron Corporation; Canton, Mass., USA) for around 10 seconds to enhance the stabilization further. The metal cap was removed and the sample set-aside on the bench top for around 30 minutes before they were placed in a humidor at 37° C. for 24 hours.

The bonded metal buttons were sheared off with a knife-edged blade at a crosshead speed of 0.5 mm/min using a universal testing machine (Instron Corporation; Canton, Mass., USA). The force needed to break the bond is divided by the bonded are. The shear bond strength is reported in Newton.mm².

TABLE 5

Film thickness (μm) and shear bond strength (SBS) in MPa of crown and bridge cements.

| PMGDM (%) | DCPA (wt %) | film thickness | SBS bulk | SBS metal |
|---|---|---|---|---|
| 17 | 47 | 16 | 2.5 ± 2.2 | 1.5 ± 0.5 |
| 17 | 42.5 | 18 | 3.3 ± 3.0 | 1.9 ± 0.4 |
| 17 | 33 | 17 | 1.8 ± 1.7 | 1.2 ± 0.3 |
| 25 | 47 | 19 | 0.9 ± 1.2 | 2.2 ± 0.7 |
| 25 | 42.5 | 19 | 0.9 ± 0.8 | 2.0 ± 0.7 |
| 25 | 33 | 17 | 0.6 ± 0.2 | 1.8 ± 0.8 |
| 36 | 47 | 27 | 3.2 ± 2.2 | 3.2 ± 0.8 |
| 38 | 42.5 | 23 | 2.5 ± 1.6 | 2.8 ± 0.6 |
| 38 | 33 | 20 | 2.5 ± 1.9 | 3.4 ± 0.4 |
| control Multilink (Ivoclar-Vivadent) | | 15 | N/A | 2.0 ± 1.6 |
| control Rely X (3M) | | 28 | 3.3 ± 1.9 | 0.9 ± 0.7 |

EXAMPLE 6

Additional Cement Embodiments

TABLE 6

Formulation b151-80a.

| | paste A wt % | paste B wt % | total wt % | cement wt % |
|---|---|---|---|---|
| TEGDMA | 9.5 | 2.5 | 12 | 6 |
| PMGDM | 0 | 75 | 75 | 37.5 |
| UDMA | 35 | 0 | 35 | 17.5 |
| DCPA | 55 | 20 | 75 | 37.5 |
| TTCP | 0 | 0 | 0 | 0 |
| SILICA | 0 | 0 | 0 | 0 |
| CQ | 0.1 | 0.2 | 0.3 | 0.15 |
| DMAPE | 0.4 | 0 | 0.4 | 0.2 |
| BHT | 0 | 0.3 | 0.3 | 0.15 |
| BPO | 0 | 2 | 2 | 1 |
| TOTAL | 100 | 100 | 200 | 100 |

% adhesive resin in the resin component = 61.5
Film Thickness: 23 μm
Flexure Strength: 51.4 ± 8.4 MPa
Bond Strength (±150 N) = 2.5 ± 1.6 mm

TABLE 7

Formulation B 151-77a.

| | paste A wt % | paste B wt % | total wt % | cement wt % |
|---|---|---|---|---|
| TEGDMA | 9.5 | 5.5 | 15 | 7.5 |
| PMGDM | 0 | 33 | 33 | 16.5 |
| UDMA | 45 | 10 | 55 | 27.5 |
| DCPA | 45 | 49 | 94 | 47 |
| TTCP | 0 | 0 | 0 | 0 |
| SILICA | 0 | 0 | 0 | 0 |
| CQ | 0.1 | 0.2 | 0.3 | 0.15 |
| DMAPE | 0.4 | 0 | 0.4 | 0.2 |
| BHT | | 0.3 | 0.3 | 0.15 |
| BPO | | 2 | 2 | 1 |
| TOTAL | 100 | 100 | 200 | 100 |

% adhesive resin in the resin component = 32.0
Film Thickness: 18 ± 1.4 μm
Bond Strength (±150 N) = 2.47 ± 2.2
Flexure Strength: 49.2 ± 8.5 MPa

TABLE 8

Formulation 80c.

| | paste A wt % | paste B wt % | total wt % | cement wt % |
|---|---|---|---|---|
| TEGDMA | 10.5 | 2.5 | 13 | 6.5 |
| PMGDM | 0 | 75 | 75 | 37.5 |
| UDMA | 34 | 10 | 44 | 22 |
| DCPA | 55 | 10 | 65 | 32.5 |
| TTCP | 0 | 0 | 0 | 0 |
| SILICA | 0 | 0 | 0 | 0 |
| CQ | 0.1 | 0.2 | 0.3 | 0.15 |
| DMAPE | 0.4 | 0 | 0.4 | 0.2 |
| BHT | 0 | 0.3 | 0.3 | 0.15 |
| BPO | 0 | 2 | 2 | 1 |
| TOTAL | 100 | 100 | 200 | 100 |

% adhesive resin in the resin component = 56.8
Film Thickness = 20 μm
Bond Strength (±150 N) = 2.5 ± 1.9
Flexure Strength: 46.4 MPa

TABLE 9

| | Formulation 41B | | | | |
|---|---|---|---|---|---|
| paste A | | paste B | | cement | |
| | wt % | | wt % | | wt % |
| TEGDMA | 4.5 | TEGDMA | 5.5 | | 5 |
| PMGDM | 0 | PMGDM | 10 | | 5 |
| UDMA | 50 | UDMA | 32 | | 41 |
| DCPA | 5 | DCPA | 25 | | 15 |
| TTCP | 40 | TTCP | 26 | | 33 |
| SILICA | 0 | SILICA | 0 | | 0 |
| CQ | 0.2 | CQ | 0.2 | | 0.2 |
| DMAPE | 0.3 | DMAPE | 0 | | 0.15 |
| | | BHT | 0.3 | | 0.15 |
| | | BPO | 1 | | 0.5 |

% adhesive resin in the resin component = 10.9

3-point flexure strength: 50.8 ± 3.4 MPa

Film Thickness: 31.3 μm

Mole ratio TTCP:DCPA 0.82

The invention claimed is:

1. A remineralizing dental cement preparation which comprises two pastes, wherein:
    (a) paste A comprises:
        about 10% by weight triethyleneglycol dimethacrylate;
        about 28% by weight urethane dimethacrylate;
        about 61% by weight dicalcium phosphate anhydrous;
        about 0.5% by weight 2-(4-dimethyl-aminophenyl) ethanol;
        about 0.2% by weight camphoroquinone; and
    (b) paste B comprises:
        about 31% by weight pyromelletic glycerol dimethacrylate;
        about 6% by weight triethyleneglycol dimethacrylate;
        about 59% by weight dicalcium phosphate anhydrous;
        about 0.2% by weight camphoroquinone;
        about 3% by weight benzoyl peroxide; and
        about 0.03% by weight 2,6-di-t-butyl-4-methyl phenol.

2. The remineralizing dental cement preparation of claim 1 wherein paste A further comprises sodium hexafluorosilicate.

3. A method of making the remineralizing dental cement of claim 1 comprising mixing a paste A with a paste B.

4. The method of claim 1 wherein paste A further comprises sodium hexafluorosilicate.

* * * * *

UNITED STATES PATENT AND TRADEMARK OFFICE
CERTIFICATE OF CORRECTION

| | | |
|---|---|---|
| PATENT NO. | : 7,619,016 B2 | Page 1 of 1 |
| APPLICATION NO. | : 10/883011 | |
| DATED | : November 17, 2009 | |
| INVENTOR(S) | : Dickens et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 997 days.

Signed and Sealed this
Twenty-eighth Day of December, 2010

David J. Kappos
*Director of the United States Patent and Trademark Office*